(12) United States Patent
Kim et al.

(10) Patent No.: US 10,186,884 B2
(45) Date of Patent: Jan. 22, 2019

(54) CHARGING APPARATUS FOR MOBILE DEVICE AND MULTI-STATION CHARGING APPARATUS USING THE SAME

(71) Applicant: SEOUL VIOSYS CO., LTD., Ansan-si (KR)

(72) Inventors: Jong-Rack Kim, Seoul (KR); Seong-Min Lee, Seoul (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 15/696,617

(22) Filed: Sep. 6, 2017

(65) Prior Publication Data
US 2017/0373516 A1    Dec. 28, 2017

Related U.S. Application Data

(63) Continuation of application No. 14/541,538, filed on Nov. 14, 2014, now Pat. No. 9,787,113.

(30) Foreign Application Priority Data

Nov. 15, 2013  (KR) .................. 10-2013-0138717
Sep. 5, 2014   (KR) .................. 10-2014-0118850

(51) Int. Cl.
| H02J 7/00 | (2006.01) |
| F21V 7/00 | (2006.01) |
| F21V 8/00 | (2006.01) |
| A61L 2/10 | (2006.01) |
| F21Y 115/10 | (2016.01) |

(52) U.S. Cl.
CPC .............. *H02J 7/0044* (2013.01); *A61L 2/10* (2013.01); *F21V 7/0066* (2013.01); *G02B 6/0075* (2013.01); *F21Y 2115/10* (2016.08)

(58) Field of Classification Search
CPC .................................. H02J 7/0044; A61L 2/10
USPC ............................ 320/107, 115; 250/455.11
See application file for complete search history.

(56) References Cited

U.S. PATENT DOCUMENTS

| 8,481,970 B2 | 7/2013 | Cooper et al. |
| 8,964,405 B2 | 2/2015 | La Porte et al. |
| 9,787,113 B2 * | 10/2017 | Kim .................. H02J 7/0044 |
| 2005/0255895 A1 | 11/2005 | Lee et al. |
| 2010/0044582 A1 * | 2/2010 | Cooper ................ A61L 2/10 |
| | | 250/455.11 |

FOREIGN PATENT DOCUMENTS

| CN | 101202457 A | 6/2008 |
| CN | 201638104 U | 11/2010 |

(Continued)

OTHER PUBLICATIONS

First Office Action in Chinese Patent Application No. 201410652673.5, dated Jun. 22, 2016 (with English translation).

*Primary Examiner* — Edward Tso
*Assistant Examiner* — Aaron Piggush
(74) *Attorney, Agent, or Firm* — Perkins Coie LLP

(57) ABSTRACT

A charging apparatus for a mobile device includes a charging apparatus case having a slot into which a mobile device is inserted and mounted, wherein the front and rear surfaces of the mobile device are exposed in the slot; and a UV light source configured to irradiate UV light onto the front and rear surfaces of the mobile device, which are exposed in the slot.

18 Claims, 9 Drawing Sheets

(56) References Cited

FOREIGN PATENT DOCUMENTS

| | | |
|---|---|---|
| CN | 202142883 U | 2/2012 |
| CN | 202353246 U | 7/2012 |
| CN | 202605362 U | 12/2012 |
| CN | 203707444 U | 7/2014 |
| KR | 20110083073 A | 7/2011 |
| WO | 2006022466 A1 | 3/2006 |

\* cited by examiner

CHARGING APPARATUS FOR MOBILE DEVICE AND MULTI-STATION CHARGING APPARATUS USING THE SAME

CROSS REFERENCE TO RELATED APPLICATION

This application is a continuation of and claims the benefit of priority to U.S. patent application Ser. No. 14/541,538, filed in Nov. 14, 2014, which claims the benefit of Korean Patent Application No. 10-2013-0138717, filed on Nov. 15, 2013, and Korean Patent Application No. 10-2014-0118850, filed on Sep. 5, 2014, which are hereby incorporated by reference in their entirety into this application.

BACKGROUND

1. Technical Field

The present disclosure relates to a charging apparatus for a mobile device, and more particularly, to a charging apparatus for a mobile device, which has an improved sterilization function, and a multi-station charging apparatus using the same.

2. Related Art

Recently, as various mobile devices are rapidly spread, development for charging apparatuses capable of charging mobile devices has been actively conducted. The charging apparatuses for a mobile device may be classified into a wired charging type and a wireless charging type. In either type, a mobile device is charged in a state where the mobile device is supported by a support.

Most charging apparatuses for a mobile device have a structure in which a wired port or a wireless port is arranged adjacent to the lower end thereof and a support for supporting a mobile device is arranged to be inclined by a predetermined angle. In such charging apparatuses for a mobile device, the mobile device is charged through the wired port or wireless port in a state where the mobile device is mounted such that the rear surface thereof is brought into contact with the surface of the support. The mobile device mounted on a charging apparatus in this way is exposed only on the front surface thereof. Therefore, even when sterilization treatment is performed for the mobile device while the mobile device is mounted on the charging apparatus, sterilization cannot help but be carried out in a restricted manner only on the front surface of the mobile device, by which a limitation is caused.

SUMMARY

Various embodiments are directed to a charging apparatus for a mobile device, which is capable of simultaneously sterilizing both surfaces of a mobile device in a state where the mobile device is mounted on the charging apparatus, and a multi-station charging apparatus using the same.

In an embodiment, a charging apparatus for a mobile device may include: a charging apparatus case having a slot into which a mobile device is inserted and mounted, wherein the front and rear surfaces of the mobile device are exposed in the slot; and a UV light source configured to irradiate UV light onto the front and rear surfaces of the mobile device, which are exposed in the slot.

The charging apparatus may further include a charging port arranged at the bottom of the charging apparatus case.

The charging port may include any one of a wired charging port and a wireless charging port.

The case may have a slide dock installed therein, the slide dock moving between an inner predetermined position of the case and the outside, and the charging port may be installed on the slide dock. A charging terminal installed on the slide dock is exposed to the outside in a state where the slide dock is drawn to the outside from the case. The charging apparatus may further include a stopper interworking with the movement of the slide dock. When the slide dock is drawn to the outside from the case, the stopper may be positioned in a slot having no corresponding charging terminal.

The slot may have a guide installed therein so as to guide an object to the charging port, and the guide may be formed of a material transmitting UV light.

The charging port may be installed on a rotating drum which rotates about an axis. When the rotating drum is rotated, the mobile device connected to the charging port may be rotated together to be obliquely placed in the slot. The rotating drum may be installed on the slide dock. The rotating drum may be rotated between at least first and second positions, and have an elastic body installed thereon, the elastic body elastically supporting the rotating drum in a direction where the rotating drum is rotated from the second position to the first position. The rotating drum may be rotated between at least first and second positions, and include a power supply trigger device which is triggered to supply power to the UV light source when the rotating drum is located at the second position.

Any one of the case and the slide dock, which are moved relatively with each other, may have a power supply rail installed thereon, and the other one may have power connection units connected to the UV light sources arranged in the slot. According to the relative position between the case and the slide dock, the power connection units may be contacted with or isolated from the power supply rail. The UV light source may include a UV LED. The charging apparatus may further include a secondary optic provided at the front of the UV light source and configured to control the diffusion angle and beam angle of the UV light source.

The UV light source may emit UV light at a wavelength of 100 nm to 400 nm.

The UV light source may include: a first UV light source arranged on an inner wall facing the front surface of the mobile device, among the inner walls of the slot, and configured to irradiate UV light onto the front surface of the mobile device; and a second UV light source arranged on an inner wall facing the rear surface of the mobile device, among the inner walls of the slot, and configured to irradiate UV light onto the rear surface of the mobile device. The first UV light source may be arranged at one or more of the corners of the inner wall facing the front surface of the mobile device. The second UV light source may be arranged at one or more of the corners of the inner wall facing the rear surface of the mobile device.

The UV light source may include: a first UV light source arranged on one inner side wall facing one side surface of the mobile device, among the inner side walls of the slot; and a second UV light source arranged on the other inner side wall facing the other side surface of the mobile device, among the inner side walls of the slot. In this case, the charging apparatus may further include: a first reflecting plate arranged on an inner wall of the slot, facing the rear surface of the mobile device, and configured to reflect UV light to the rear surface of the mobile device; and a second reflecting plate arranged on an inner wall of the slot, facing the front surface of the mobile device, and configured to reflect UV light to the front surface of the mobile device.

The UV light source may include: a first UV light source arranged at a first corner of an inner wall of the slot such that UV light has a path parallel to the rear surface of the mobile device; and a second UV light source arranged at a second corner of an inner wall of the slot such that UV light has a path parallel to the front surface of the mobile device. In this case, the charging apparatus may further include: a first light guide plate arranged on an inner wall of the slot, facing the rear surface of the mobile device, and configured to guide UV light emitted from the first UV light source such that the UV light is surface-emitted onto the rear surface of the mobile device; and a second light guide plate arranged on an inner wall of the slot, facing the front surface of the mobile device, and configured to guide UV light emitted from the second UV light source such that the UV light is surfaced-emitted onto the front surface of the mobile device.

The UV light source may be installed on an inner side surface of the slot so as to face a side surface of an object, and installed close to any one of the front and rear surfaces of the object.

The charging apparatus may further include a power supply trigger device configured to control power to be automatically supplied to the UV light source when the mobile device is mounted in the slot. The charging apparatus may further include an openable and closable door to expose or cover the slot, and power may be supplied to the UV light source arranged in the slot in a state where the power supply trigger device is operated and the door is closed.

The charging apparatus may further include a support for supporting the mobile device such that the mobile device is mounted upright in the slot.

In an embodiment, a multi-station charging apparatus for a mobile device may include: a charging apparatus case having a slot into which a mobile device is inserted and mounted, wherein the front and rear surfaces of the mobile device are exposed in the slot; a multi-station device arranged at both side surfaces of the slot; and a UV light source configured to irradiate UV light onto the front and rear surfaces of the mobile device, which are exposed in the slot.

The multi-station charging apparatus may further include a charging port arranged at the bottom of the charging apparatus case. The charging port may include any one of a wired charging port and a wireless charging port.

The UV light source may include a UV LED.

The UV light source may emit UV light at a wavelength of 100 nm to 400 nm.

The UV light source may include: a first UV light source arranged on an inner wall facing the front surface of the mobile device, among the inner walls of the slot, and configured to irradiate UV light onto the front surface of the mobile device; and a second UV light source arranged on an inner wall facing the rear surface of the mobile device, among the inner walls of the slot, and configured to irradiate UV light onto the rear surface of the mobile device. The first UV light source may be arranged at one or more of the corners of the inner wall facing the front surface of the mobile device. The second UV light source may be arranged at one or more of the corners of the inner wall facing the rear surface of the mobile device.

The UV light source may include: a first UV light source arranged on one inner side wall facing one side surface of the mobile device, among the inner side walls of the slot; and a second UV light source arranged on the other inner side wall facing the other side surface of the mobile device, among the inner side walls of the slot. In this case, the multi-station charging apparatus may further include: a first reflecting plate arranged on an inner wall of the slot, facing the rear surface of the mobile device, and configured to reflect UV light to the rear surface of the mobile device; and a second reflecting plate arranged on the inner wall of the slot, facing the front surface of the mobile device, and configured to reflect UV light to the front surface of the mobile device.

The UV light source may include: a first UV light source arranged at a first corner of an inner wall of the slot such that UV light has a path parallel to the rear surface of the mobile device; and a second UV light source arranged at a second corner of an inner wall of the slot such that UV light has a path parallel to the front surface of the mobile device. In this case, the multi-station charging apparatus may further include: a first light guide plate arranged on an inner wall of the slot, facing the rear surface of the mobile device, and configured to guide UV light emitted from the first UV light source such that the UV light is surface-emitted onto the rear surface of the mobile device; and a second light guide plate arranged on an inner wall of the slot, facing the front surface of the mobile device, and configured to guide UV light emitted from the second UV light source such that the UV light is surface-emitted onto the front surface of the mobile device.

The multi-station charging apparatus may further include a power supply trigger device configured to control power to be automatically supplied to the UV light source, when the mobile device is mounted in the slot.

The multi-station charging apparatus may further include a support for supporting the mobile device such that the mobile device is upright mounted in the slot.

The multi-station device may include a speaker.

DETAILED DESCRIPTION

Figure 1:
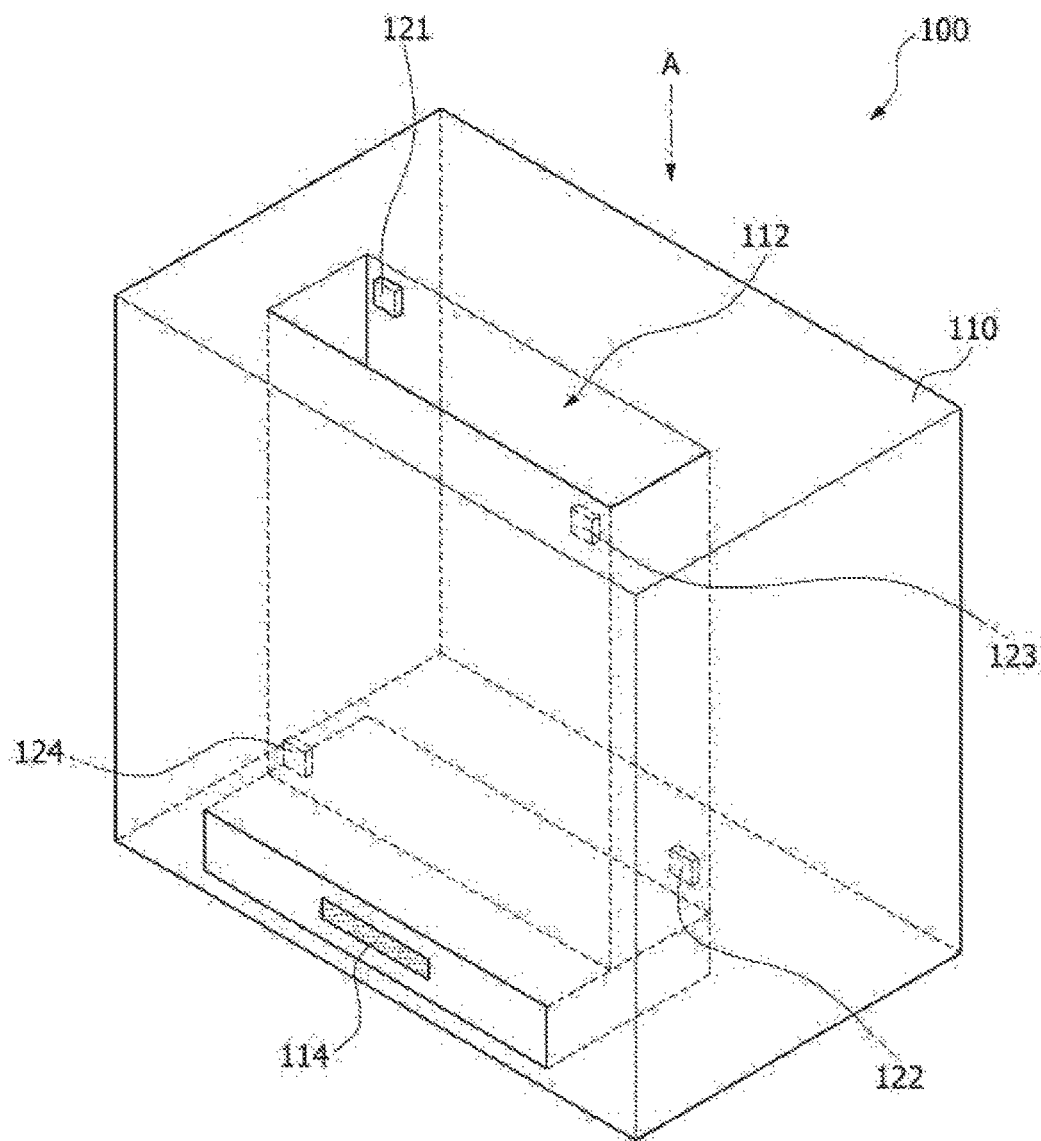
FIG. 1 is a diagram illustrating a charging apparatus for a mobile device in accordance with an embodiment of the present invention.

Exemplary embodiments will be described below in more detail with reference to the accompanying drawings. The disclosure may, however, be embodied in different forms and should not be constructed as limited to the embodiments set forth herein. Rather, these embodiments are provided so that this disclosure will be thorough and complete, and will fully convey the scope of the disclosure to those skilled in the art. Throughout the disclosure, like reference numerals refer to like parts throughout the various figures and embodiments of the disclosure.

First Embodiment

Figure 2:
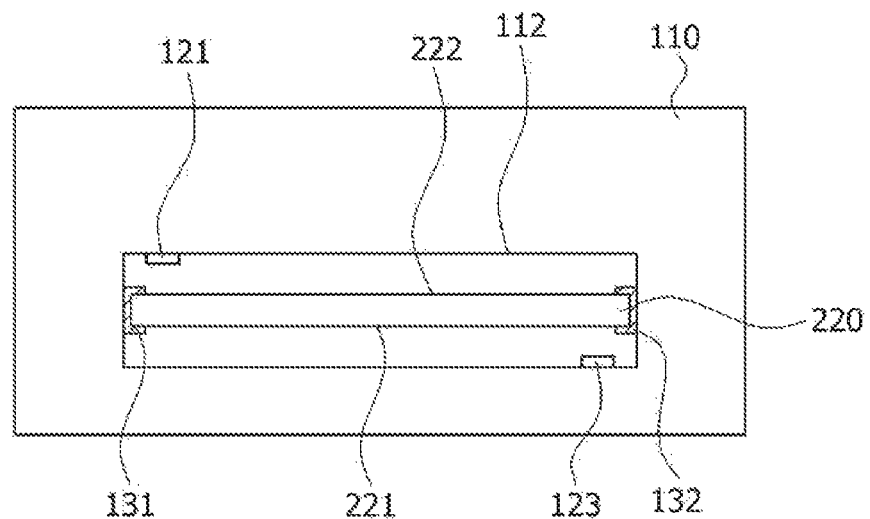
FIG. 2 is a diagram illustrating the shape of the charging apparatus for a mobile device, when seen from a direction A of FIG. 1.

FIG. 1 is a diagram illustrating a charging apparatus for a mobile device in accordance with an embodiment of the present invention. FIG. 2 is a diagram illustrating the shape of the charging apparatus for a mobile device, when seen from a direction A of FIG. 1.

Referring to FIGS. 1 and 2, the charging apparatus 100 for a mobile device in accordance with the embodiment of the present invention may include a charging apparatus case 110 having a slot 112 into which a mobile device 220 is inserted and mounted. In the present embodiment, the mobile device 220 is inserted and mounted in the slot 112, but this is only an example. The present invention may be applied to the case in which a mobile device is mounted through a front door, for example. Furthermore, FIG. 1 illustrates that the slot 112 is opened upward at all times. However, an openable and closable door may be further provided at the top of the slot 112. Furthermore, the charge apparatus case 110 has a rectangular box shape, but may be formed in another shape. In the present embodiment, the mobile device 220 inserted and mounted in the slot 112 may be placed upright as illustrated in FIG. 1, and both of the front and rear surfaces 221 and 222 of the mobile device 220 may be exposed as illustrated in FIG. 2. That is, the front surface 221 of the mobile device 220 may be separated at a predetermined interval from the inner wall of the slot 112, and the rear surface 222 of the mobile device 220 may also be separated at a predetermined interval from the inner wall of the slot 112.

The mobile device 220 may be supported by supports 131 and 132. The supports 131 and 132 may support both side surfaces of the mobile device 220 such that the mobile device 220 is mounted upright. The supports 131 and 132 may be formed of a material transmitting UV light, for example, PMMA having a high monomer ratio. The mobile device 220 may be supported in another method. For example, the bottom of the mobile device 220 may be detachably supported. In either case, as the mobile device 220 is inserted into the slot 112, the mobile device 220 may be fixed and supported. In this state, when the mobile device 220 is pressed, the mobile device 220 may be released to protrude from the slot 112. As the mobile device 220 is inserted and mounted in the slot 112, a charging port of the mobile device 220 may be electrically connected to a charging system of the charging apparatus.

The slot 112 may have UV light sources 121, 122, 123, and 124 arranged on the inner walls thereof. The UV light sources 121, 122, 123, and 124 may include first UV light sources 121 and 122 and second UV light sources 123 and 124. The first UV light sources 121 and 122 may be arranged on an inner wall facing the rear surface of the mobile device 220, among the inner walls of the slot 112, and irradiate UV light onto the rear surface of the mobile device 220. The second UV light sources 123 and 124 may be arranged on an inner wall facing the front surface of the mobile device 220, among the inner walls of the slot 112, and irradiate UV light onto the front surface of the mobile device 220. The first UV light sources 121 and 122 may be arranged at two corners in a diagonal direction among the corners of the inner wall facing the rear surface of the mobile device 220. Similarly, the second UV light sources 123 and 124 may also be arranged at two corners in a diagonal direction among the corners of the inner wall facing the front surface of the mobile device 220. However, the number and positions of the UV light sources may be changed in various manners.

The UV light sources 121, 122, 123, and 124 may include a UV light emitting diode (LED). In this case, the UV LED may be provided as a module. The UV light sources 121, 122, 123, and 124 may emit UV light at a wavelength of 100 nm to 400 nm. The UV light emitted at a wavelength of 100 nm to 400 nm from the UV light sources 121, 122, 123, and 124 may sterilize the front and rear surfaces 221 and 222 of the mobile device 220 at the same time. Although not illustrated, a UV light reflecting plate may be additionally arranged to uniformly form irradiation paths of the UV light emitted from the UV light sources 121, 122, 123, and 124 on the front surface 221 and the rear surface 222 of the mobile device 220. When UV light sterilization is performed within a predetermined space, the rate of sterilization in the case where the UV light reflecting plate is installed on the wall surfaces defining the space is higher by 2 log than the case where the UV light reflecting plate is not installed. Furthermore, a protective layer formed of a UV light-transmitting material may be further arranged to protect the UV light sources 121, 122, 123, and 124 from external pollutants. The protective layer may include a PMMA layer having a high monomer ratio. Power for the UV light sources 121, 122, 123, and 124 may be manually supplied by a user, or automatically supplied according to whether the mobile device 220 is inserted and mounted. When the power is intended to be automatically supplied, a power supply trigger device may be arranged in the charging apparatus case 110. In this case, when the mobile device 220 is mounted in the slot 112, power may be automatically supplied to the UV light sources 121, 122, 123, and 124 by the power supply trigger device.

Furthermore, when the above-described door is provided in order to prevent UV light from being exposed to the outside and to prevent dust from being introduced into the slot, the power supply trigger device may be operated as the mobile device 200 is inserted. Furthermore, only when the door is closed, power may be supplied to the UV light sources to irradiate UV light.

The charging apparatus case 110 may have a charging port 114 arranged at the bottom thereof. In the present embodiment, the charging port 114 may be arranged at the bottom of the front surface of the charging apparatus case 110. However, this is only an example, and the charging port 114 may be arranged at another position, for example, a side surface of the charging apparatus case 110. In either case, the charging port 114 may be electrically connected to the charging system in the charging apparatus case 110. Thus, the charging port 114 may be electrically connected to the charging apparatus for the mobile device 220, for example, a battery through the charging system. The charging port 114 may include a wired charging port or wireless charging port. The charging port 114 may include both a wired charging port and a wireless charging port. Furthermore, although not illustrated, a charging terminal may be provided at a position corresponding to the position at which a charging connection terminal of the mobile device is inserted when the mobile device 220 is inserted, in case where the charging port is a wired charging terminal. In this case, the charging terminal and the connection terminal of the mobile device may be conveniently coupled to each other only by inserting the mobile device 200 along the supports 131 and 132.

Second Embodiment

Figure 3:
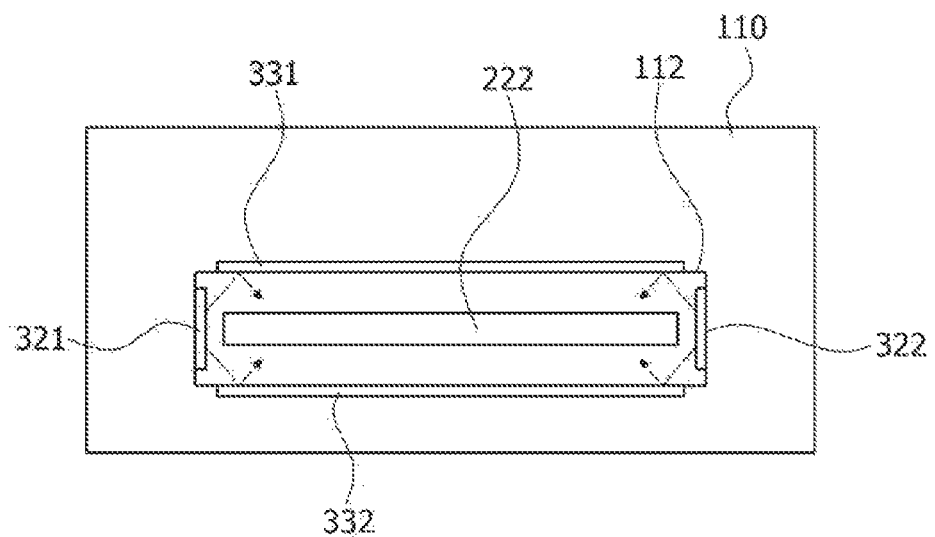
FIG. 3 is a diagram illustrating the shape of a charging apparatus for a mobile device in accordance with another embodiment of the present invention, when seen from the top.

FIG. 3 is a diagram illustrating the shape of a charging apparatus for a mobile device in accordance with another embodiment of the present invention, when seen from the top. In FIG. 3, the same reference numerals as those of FIGS. 1 and 2 represent like elements. Thus, the duplicated descriptions are omitted herein.

Referring to FIG. 3, the slot 112 may have UV light sources 321 and 322 arranged on the inner walls thereof. The UV light sources 321 and 322 may include a first UV light source 321 and a second UV light source 322. The first UV light source 321 may be arranged on a first inner wall facing one side surface of the mobile device 220, among the inner walls of the slot 112. The second UV light source 322 may be arranged on a second inner wall facing the other side surface of the mobile device 220, among the inner walls of the slot 112. Although not illustrated, a plurality of first UV light sources 321 may be vertically arranged on the first inner wall of the slot 112 so as to be separated from each other. Similarly, a plurality of second UV light sources 322 may also be vertically arranged on the second inner wall of the slot 112 so as to be separated from each other.

In the present embodiment, the slot 112 may include first and second reflecting plates 331 and 332 arranged on the inner wall facing the rear surface of the mobile device 220 and the inner wall facing the front surface of the mobile device 200, respectively. As indicated by dotted lines in the FIG. 3, the first and second reflecting plates 331 and 332 may control UV light paths to reflect UV light emitted from the first and second UV light sources 321 and 322 onto the rear and front surfaces of the mobile device 220.

The first and second UV light sources 321 and 322 may include a UV LED. In this case, the UV LED may be provided as a module. The first and second UV light sources 321 and 322 may emit UV light at a wavelength of 100 nm to 400 nm. The UV light emitted at a wavelength of 100 nm to 400 nm from the first and second UV light sources 321 and 322 may sterilize the front and rear surfaces 221 and 222 of the mobile device 220 at the same time. Although not illustrated, a protective layer formed of a UV light-transmitting material may be further arranged to protect the first and second UV light sources 321 and 322 from external pollutants. Power for the first and second UV light sources 321 and 322 may be manually supplied by a user, or automatically supplied according to whether the mobile device 220 is inserted and mounted. When power is intended to be automatically supplied, a power supply trigger device may be arranged in the charging apparatus case 110. In this case, when the mobile device 220 is mounted in the slot 112, power may be automatically supplied to the first and second UV light sources 321 and 322 by the power supply trigger device.

Third Embodiment

Figure 4:
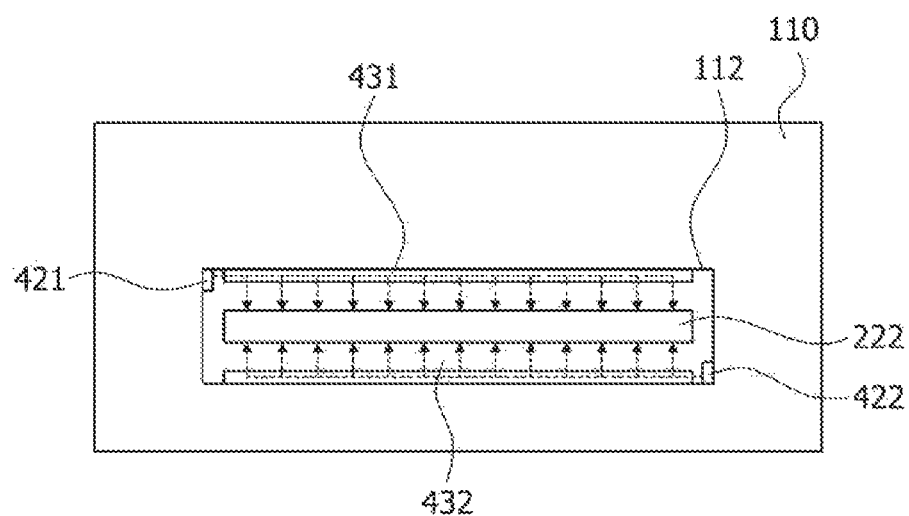
FIG. 4 is a diagram illustrating the shape of an apparatus for charging a mobile device in accordance with another embodiment of the present invention, when seen from the top.

FIG. 4 is a diagram illustrating the shape of an apparatus for charging a mobile device in accordance with another embodiment of the present invention, when seen from the top. In FIG. 4, the same reference numerals as those of FIGS. 1 and 2 represent like elements. Thus, the duplicated descriptions are omitted herein.

Referring to FIG. 4, the slot 112 may have UV light sources 421 and 422 arranged at corners facing each other on the inner walls of the slot 112. The UV light sources 421 and 422 may include a first UV light source 421 and a second UV light source 422. The first UV light source 421 may arranged at a first corner of the inner walls of the slot 112. The first UV light source 421 may be arranged in such a manner that UV light emitted from the first UV light source 421 has a path parallel to the rear surface of the mobile device 222. The second UV light source 422 may arranged at a second corner of the inner walls of the slot 112. The second UV light source 422 may be arranged in such a manner that UV light emitted from the second UV light source 422 has a path parallel to the front surface of the mobile device 222. Although not illustrated, a plurality of first UV light sources 421 may be vertically arranged at the first corner of the slot 112 so as to be separated from each other. Similarly, a plurality of second UV light sources 422 may also be vertically arranged at the second corner of the slot 112 so as to be separated from each other.

On a first inner wall facing the rear surface of the mobile device 220 and a second inner wall facing the front surface of the mobile device 200, first and second light guide plates 431 and 432 may be provided. As indicated by dotted lines in the FIG. 4, the first and second light guide plates 431 and 432 may guide UV light emitted from the first and second UV light sources 421 and 422 such that the UV light is uniformly surface-emitted onto the rear and front surfaces of the mobile device 220.

The first and second UV light sources 421 and 422 may include a UV LED. In this case, the UV LED may be provided as a module. The first and second UV light sources 421 and 422 may emit UV light at a wavelength of 100 nm to 400 nm. The UV light emitted at a wavelength of 100 nm to 400 nm from the first and second UV light sources 421 and 422 may sterilize the front and rear surfaces 221 and 222 of the mobile device 220 at the same time. Although not illustrated, a protective layer formed of a UV light-transmitting material may be further arranged to protect the first and second UV light sources 421 and 422 from external pollutants. Power for the first and second UV light sources 421 and 422 may be manually supplied by a user, or automatically supplied according to whether the mobile device 220 is inserted and mounted. When power is intended to be automatically supplied, a power supply trigger device may be arranged in the charging apparatus case 110. In this case, when the mobile device 220 is mounted in the slot 112, power may be automatically supplied to the first and second UV light sources 421 and 422 by the power supply trigger device.

Fourth Embodiment

Figure 5:
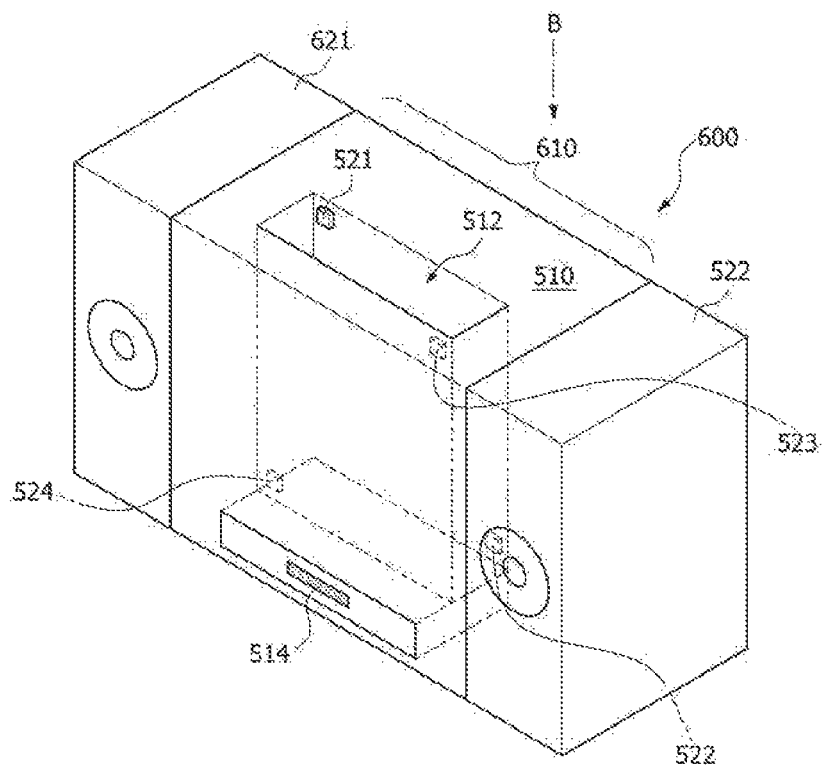
FIG. 5 is a diagram illustrating a multi-station charging apparatus for a mobile device in accordance with another embodiment of the present invention.
Figure 6:
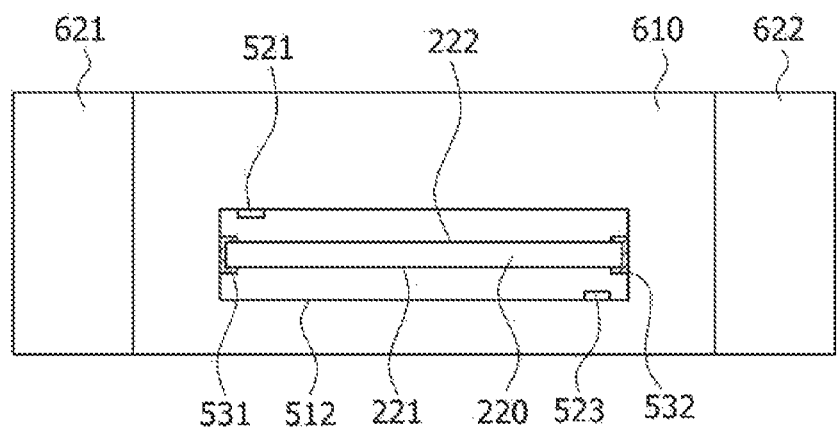
FIG. 6 is a diagram illustrating the shape of the multi-station charging apparatus for a mobile device, when seen from a direction B of FIG. 5.

FIG. 5 is a diagram illustrating a multi-station charging apparatus for a mobile device in accordance with another embodiment of the present invention. FIG. 6 is a diagram illustrating the shape of the multi-station charging apparatus for a mobile device, when seen from a direction B of FIG. 5.

Referring to FIGS. 5 and 6, the multi-station charging apparatus 600 for a mobile device in accordance with the embodiment of the present invention may include a charging apparatus case 510 and a multi-station device. The charging apparatus case 510 may have a slot 512 into which the mobile device 220 is inserted and mounted, and the multi-station device may be arranged at both sides of the slot 512. The multi-station device may include speakers 621 and 622. However, this is only an example, and the multi-station device may include other devices in addition to the speakers 621 and 622. In the present embodiment, the mobile device 220 is inserted and mounted in the slot 512, but this is only an example. The present invention may be applied to the case in which a mobile device is mounted through a front door, for example. Furthermore, the charge apparatus case 510 has a rectangular box shape, but may be formed in another shape. The front and rear surfaces 221 and 222 of the mobile device 220 inserted and mounted in the slot 512 may be exposed to the outside. That is, the front surface 221 of the mobile device 220 may be separated at a predetermined interval from the inner wall of the slot 512, and the rear surface 222 of the mobile device 220 may also be separated at a predetermined interval from the inner wall of the slot 512.

The mobile device 220 may be supported by supports 531 and 532. The supports 531 and 532 may support both side surfaces of the mobile device 220 such that the mobile device 220 is mounted upright. However, the mobile device 220 may be supported in another method. For example, the bottom of the mobile device 220 may be detachably supported. In either case, as the mobile device 220 is inserted into the slot 512, the mobile device 220 may be fixed and supported. In this state, when the mobile device 220 is pressed, the mobile device 220 may be released to protrude from the slot 512. As the mobile device 220 is inserted and mounted in the slot 512, a charging port of the mobile device 220 may be electrically connected to a charging system of the charging apparatus.

The slot 512 may have UV light sources 521, 522, 523, and 524 arranged on the inner wall thereof. The UV light sources 521, 522, 523, and 524 may include first UV light sources 521 and 522 and second UV light sources 523 and 524. The first UV light sources 521 and 522 may be arranged on an inner wall facing the rear surface of the mobile device 220, among the inner walls of the slot 512, and irradiate UV light onto the rear surface of the mobile device 220. The second UV light sources 523 and 524 may be arranged on an inner wall facing the front surface of the mobile device 220, among the inner walls of the slot 512, and irradiate UV light onto the front surface of the mobile device 220. The first UV light sources 521 and 522 may be arranged at two corners in a diagonal direction among the corners of the inner wall facing the rear surface of the mobile device 220. Similarly, the second UV light sources 523 and 524 may also be arranged at two corners in a diagonal direction among the corners of the inner wall facing the front surface of the mobile device 220. However, the number and positions of the UV light sources may be changed in various manners. In the multi-station charging apparatus for a mobile device in accordance with the embodiment of the present invention, the UV light sources may be arranged according to the structure described with reference to FIGS. 3 and 4.

The UV light sources 521, 522, 523, and 524 may include a UV LED. In this case, the UV LED may be provided as a module. The UV light sources 521, 522, 523, and 524 may emit UV light at a wavelength of 100 nm to 400 nm. The UV light emitted at a wavelength of 100 nm to 400 nm from the UV light sources 521, 522, 523, and 524 may sterilize the front and rear surfaces 221 and 222 of the mobile device 220 at the same time. Although not illustrated, a UV light reflecting plate may be additionally arranged to uniform form irradiation paths of the UV light emitted from the UV light sources 521, 522, 523, and 524 on the front surface 221 and the rear surface 222 of the mobile device 220. Furthermore, a protective layer formed of a UV light-transmitting material may be further arranged to protect the UV light sources 521, 522, 523, and 524 from external pollutants. Power for the UV light sources 521, 522, 523, and 524 may be manually supplied by a user, or automatically supplied according to whether the mobile device 220 is inserted and mounted. When the power is intended to automatically supplied, a power supply trigger device may be arranged in the charging apparatus case 510. In this case, when the mobile device 220 is mounted in the slot 512, power may be automatically supplied to the UV light sources 521, 522, 523, and 524 by the power supply trigger device.

The charging apparatus case 510 may have a charging port 514 arranged at the bottom thereof. In the present embodiment, the charging port 514 may be arranged at the bottom of the front surface of the charging apparatus case 510. However, this is only an example, and the charging port 514 may be arranged at another position of the charging apparatus case 510. In either case, the charging port 514 may be electrically connected to the charging system in the charging apparatus case 510. Thus, the charging port 514 may be electrically connected to the charging apparatus for the mobile device 220, for example, a battery through the charging system. The charging port 514 may include a wired charging port or wireless charging port. The charging port 514 may include both a wired charging port and a wireless charging port.

Fifth Embodiment

Figure 7:
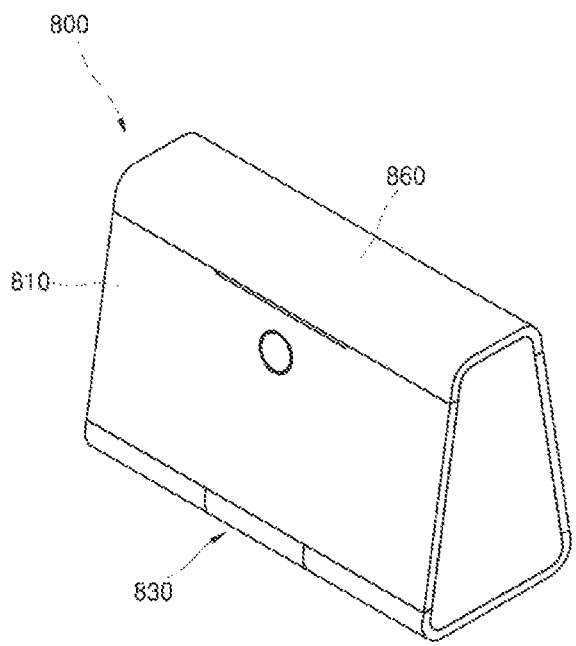
FIG. 7 is a perspective view of a charging apparatus for a mobile device in accordance with an embodiment of the present invention.
Figure 8:
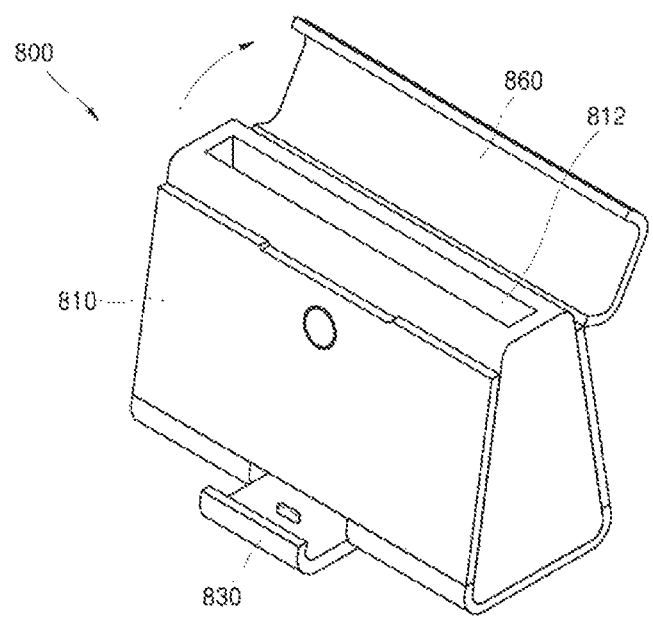
FIG. 8 is a perspective view illustrating a state in which a door of the charging apparatus for a mobile device is opened and a slide dock is drawn forward.
Figure 9:
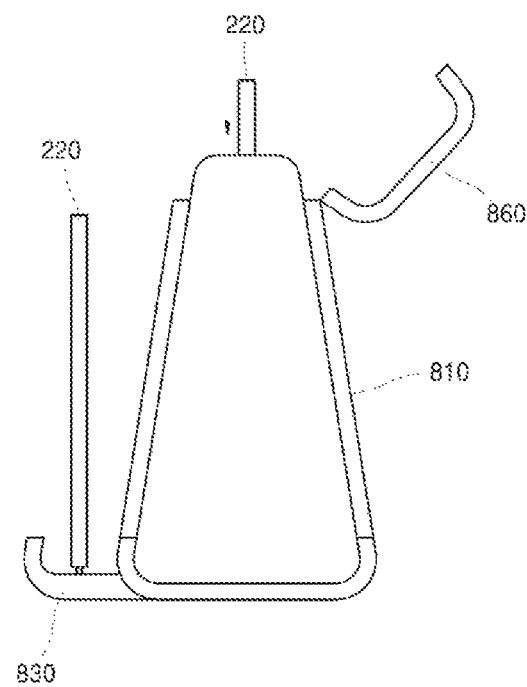
FIG. 9 is a side view illustrating that a mobile device is inserted into the charging apparatus of FIG. 8.
Figure 10:
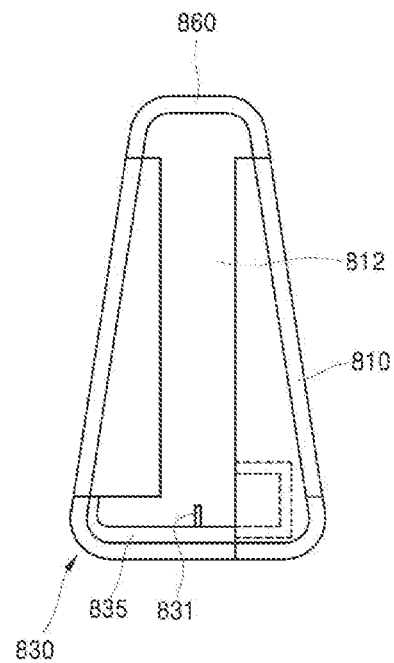
FIG. 10 is a side cross-sectional view of an intermediate part of the charging apparatus of FIG. 7.
Figure 11:
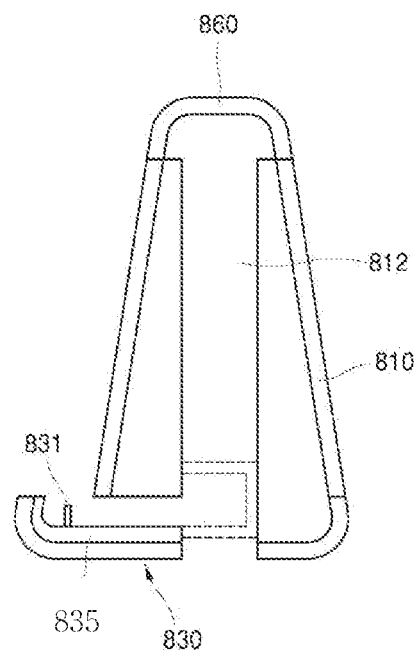
FIG. 11 is a side cross-sectional view illustrating a state in which the slide dock of the charging apparatus of FIG. 10 is drawn forward.
Figure 12:
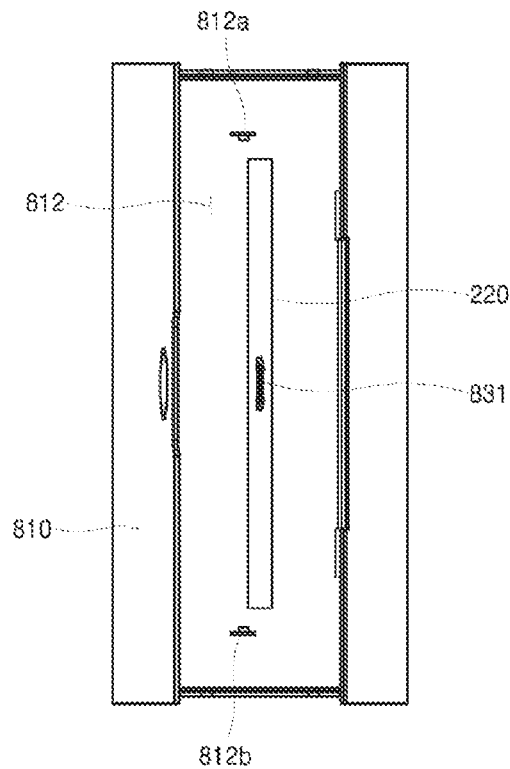
FIG. 12 is a plan view illustrating the inside of a slot in a state where the door of the charging apparatus of FIG. 7 is removed.

FIG. 7 is a perspective view of a charging apparatus for a mobile device in accordance with an embodiment of the present invention. FIG. 8 is a perspective view illustrating a state in which a door of the charging apparatus for a mobile device is opened and a slide dock is drawn forward. FIG. 9 is a side view illustrating that a mobile device is inserted into the charging apparatus of FIG. 8. FIG. 10 is a side cross-sectional view of an intermediate part of the charging apparatus of FIG. 7. FIG. 11 is a side cross-sectional view illustrating a state in which the slide dock of the charging apparatus of FIG. 10 is drawn forward. FIG. 12 is a plan view illustrating the inside of a slot in a state where the door of the charging apparatus of FIG. 7 is removed.

Referring to FIGS. 7 and 11, the charging apparatus 800 for a mobile device in accordance with the embodiment of the present invention may include a case 810, a door 860 covering the top of the case 810, and a charging unit 830 formed at the bottom of the case 810. The door 860 may be turned about one point of the rear top surface of the case 810 so as to be opened back. The charging unit 830 may include a slide dock 835 which is drawn forward from the bottom of the case or pushed into the bottom of the case.

The top of the case may be opened. When the door 860 is turned, the top of the case may be exposed. The slot 812 may be provided at the exposed top surface of the case. The slot 812 may include a UV light reflecting plate installed on the inner surface thereof.

As illustrated in FIG. 9, the mobile device 220 may be placed in the slot 812 or on the slide dock 835 drawn forward.

As illustrated in FIG. 10, the slot 812 may be housed in the case 810, and the top of the slot 812 may be opened. The slot 812 may have a charging terminal 831 provided at the bottom thereof, and the charging terminal 831 can be attached to and detached from a charging connection terminal of the mobile device 220. Since the charging terminal is positioned at the middle of the bottom of the slot in the front and rear direction of the slot, a predetermined interval may be formed between the inner wall of the slot and the front or rear surface of the mobile device in a state where the mobile device is coupled to the charging terminal. Although not illustrated in FIGS. 10 and 11, a guide formed of a material capable of transmitting UV light may be provided in the slot so as to guide the mobile device to the charging terminal.

As illustrated in FIGS. 10 and 11, the charging terminal 831 may be installed on the slide dock 835. When the slide dock 835 is pushed into the case, the charging terminal 831 and the slot 812 may be aligned with each other as illustrated in FIG. 10. Furthermore, when slide dock 835 is drawn forward, the charging terminal 831 may be exposed to the front of the case as illustrated in FIG. 11.

Regardless of whether the slide dock 835 is pushed into or drawn out of the case or whether the door 860 is opened or closed, power may be supplied to the charging terminal 831 at all times. Thus, when the slide dock 835 is pushed into the case as illustrated in FIG. 10, the mobile device may be charged in a state where the mobile device is placed in the slot. Furthermore, when the slide dock 835 is drawn out of the case as illustrated in FIG. 11, the mobile device may be charged in a state where the mobile device is placed on the charging terminal 831 exposed to the front of the case.

In order to prevent a mobile device from being inserted deeply into the slot 812 and to intuitively inform a user that the slot cannot be used, when the slide dock 835 is drawn forward, a stopper indicated by a dotted line in FIGS. 10 and 11 may be moved together with the slide dock 835 or operated in connection with the operation of the slide dock 835. When the stopper is positioned in the slot, the insertion of the mobile device 220 may be restricted. Thus, the user may intuitively recognize that the mobile device cannot be charged through the slot.

Although not illustrated, another charging terminal may be further provided at the rear side of the charging terminal 831, that is, at the position indicated by the dotted lines in FIGS. 10 and 11), instead of the stopper illustrated in FIGS. 10 and 11. In this case, when the slide dock is drawn forward, the charging terminal 831 may be exposed to the front, and the other charging terminal may be aligned with the slot. In another embodiment, the charging terminal 831 may be fixed to be aligned with the slot, and another charging terminal to be drawn may be provided at the front of the charging terminal 831. In this case, when the slide dock is drawn forward, only the charging terminal to be drawn may be drawn forward with the slide dock. Furthermore, as long as such an embodiment is proposed through the present invention, various embodiments may be provided based on such an embodiment. Furthermore, such a charging terminal is illustrated as a wired port in the drawings. However, the charging terminal may be implemented with a wireless port.

Referring to FIG. 12, a plurality of first and second UV light sources 812*a* and 812*b* may be vertically arranged on both inner surfaces of the slot 812 so as to irradiate UV light toward an object. As illustrated in FIG. 12, the first and second UV light sources may not be arranged at the center of the side surface of the mobile device 220, but arranged at a position slightly forward to the front surface. This structure considers that the front surface of a mobile device such as a tablet PC or smart phone, which is more frequently touched than the rear surface thereof, has a larger number of germs or a higher pollution level than the rear surface.

Although not illustrated, a power supply trigger device, which is operated when a mobile device is placed in the slot, may be arranged in the slot. In this case, power may be supplied to the UV light sources only in a state where the mobile device is placed in the slot, or supplied to the UV light sources only in a state where the door 850 is closed while the mobile device is placed in the slot.

Sixth Embodiment

Figure 13:
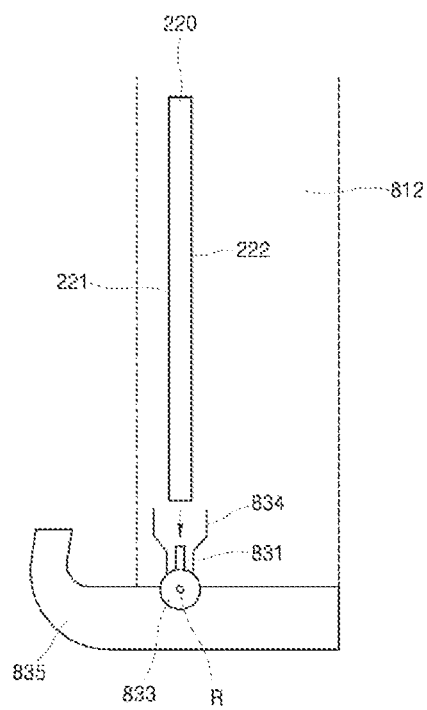
FIGS. 13 and 14 are side views illustrating a slide dock in accordance with another embodiment of the present invention.
Figure 14:
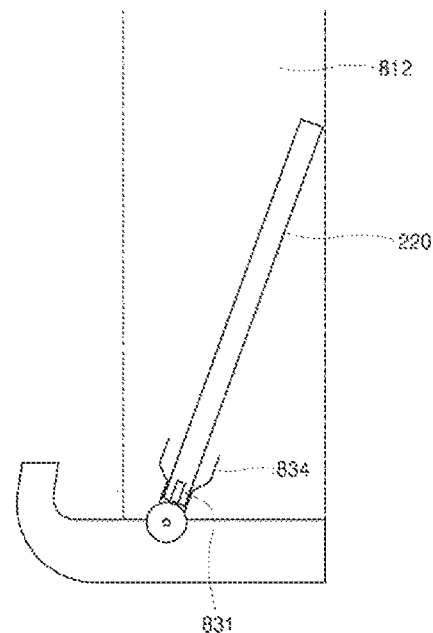
Figure 15:
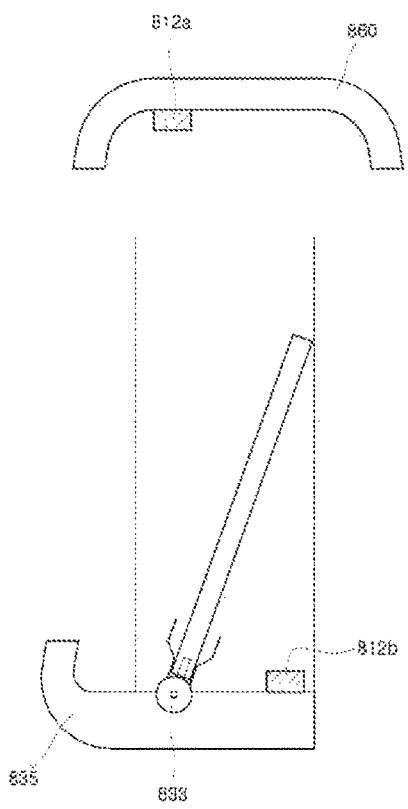
FIGS. 15 and 16 are side cross-sectional views illustrating the arrangement positions of UV light sources in the charging apparatus of FIG. 7.
Figure 16:
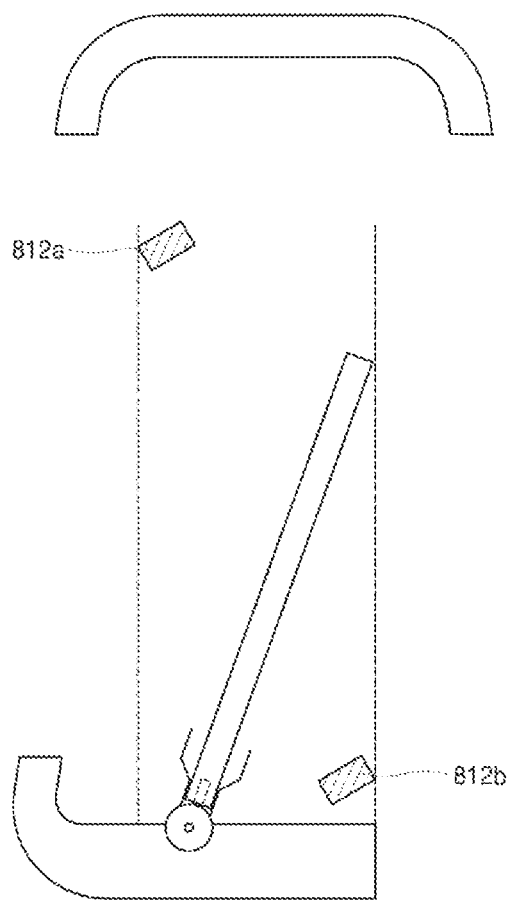
Figure 17:
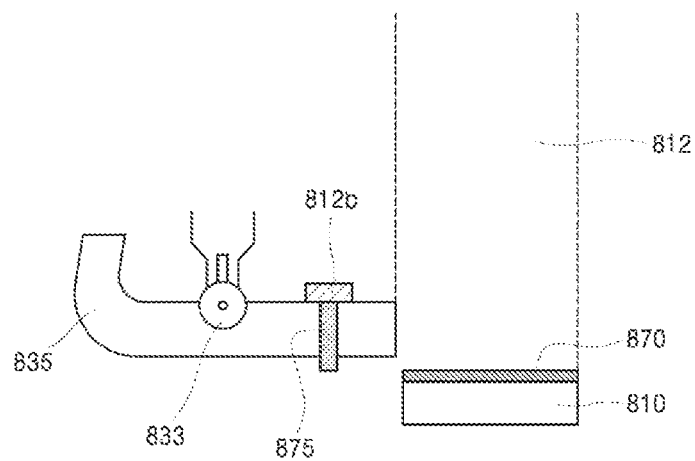
FIG. 17 is a diagram illustrating a power supply control structure in accordance with an embodiment of the present invention.

FIGS. 13 and 14 are side views illustrating a slide dock in accordance with another embodiment of the present invention. FIGS. 15 and 16 are side cross-sectional views illustrating the arrangement positions of UV light sources in the charging apparatus of FIG. 7. FIG. 17 is a diagram illustrating a power supply control structure in accordance with an embodiment of the present invention.

The descriptions of the structure illustrated in FIGS. 13 to 16 will be focused on differences from that of FIGS. 7 to 11.

FIGS. 13 and 14 illustrate a state in which the slide dock 835 is pushed into the case. Referring to FIGS. 13 and 14, the charging terminal 831 may be installed on a rotating drum 833 which rotates about an axis R with respect to the slide dock 835. Thus, when the rotating drum 833 is rotated, the charging terminal 831 may be rotated together as illustrated in FIG. 14. The rotating drum 833 may be rotated between the position at which the charging terminal 831 is placed upright and the position at which the charging terminal 831 is inclined backward at a predetermined angle. The rotating drum 833 may be elastically supported by an elastic body (not illustrated) so as to be rotated toward the position at which the charging terminal 831 is placed upright. If necessary, a damper may be installed in addition to the elastic body. In this case, when the rotating drum is rotated by the elastic force, the rotating drum may be slowly rotated at a controlled speed. Furthermore, the rotating drum 833 may have a guide 834 installed thereon so as to guide a mobile device to the charging terminal. The charging terminal may include a wired charging terminal and a wireless charging terminal.

Thus, when a user places the mobile device 220 at the regular position through the guide 834 while inserting the mobile device 200 into the slot 812 as illustrated in FIG. 13 and then slightly leans the mobile device 200, a moment may occur because the center of gravity of the mobile device is eccentrically positioned at the rear side of the rotation axis R. Then, such a moment may overcome the elastic force of the elastic body (not illustrated) so as to lean the mobile device 220 and the rotating drum 833 to the rear side, and the mobile device 220 may be obliquely placed as illustrated in FIG. 14. On the other hand, when the mobile device 220 is intended to be picked up, the mobile device 220 may be slightly lifted in a state of FIG. 14. Then, the rotating drum 833 may be returned to the original position of FIG. 13 by the elastic force of the elastic body (not illustrated). In such a structure, when the slide dock 835 is drawn forward to mount an object on the charging terminal exposed to the front of the case, the object may be obliquely placed to lean against the front surface of the case.

In such a structure in which the mobile device 220 is obliquely placed, a first UV light source 812a may be installed on the door 860 or installed at the top of the front inner wall of the slot, and a second UV light source 812b may be installed on the slide dock 835 or installed at the bottom of the rear inner wall of the slot, as illustrated in FIG. 15 or 16. Then, an object may be obliquely placed, and the UV light sources may be positioned in the opposite diagonal direction of the oblique direction of the object so as to irradiate UV light onto both surfaces of the object.

Such a structure, in which the mobile device is obliquely placed and the UV light sources are positioned in the opposite diagonal direction of the oblique direction of the mobile device in order to irradiate UV light on both surfaces of the mobile device, may reduce the width of the slot and reliably sterilize both surfaces of the mobile device through UV light. A structure in which an object is placed upright may require a predetermined interval between either surface of the object and the inner wall of the slot. However, in the structure in which a mobile device is obliquely placed in accordance with the embodiment of the present invention, the slot may be formed to be slimmer or smaller.

Furthermore, when UV LEDs are used as the UV light sources, a secondary optic (lens or light guide plate) may be provided at the front of the UV LEDs so as to properly control the diffusion angle and beam angle of UV light. Thus, UV light may be uniformly and efficiently irradiated on the surface of the object.

Furthermore, a power supply trigger device (not illustrated) may be integrally installed on the rotating drum 833. In this case, when the rotating drum 833 is placed upright as illustrated in FIG. 13, the power supply trigger device may not be operated. When the rotating drum 833 is rotated backward at a predetermined angle as illustrated in FIG. 14, the power supply trigger device may be operated. Then, power may be supplied only to the slot in which a mobile device is mounted on the rotating drum 833 and inclined backward, and UV light may be then irradiated onto the mobile device. Furthermore, only when the door is closed, power may be supplied to the UV light sources.

Although not illustrated, when the slide dock 835 is drawn out of the case such that the charge terminal 831 is exposed to the front of the case, no power needs to be supplied to the UV light source 812b exposed to the outside of the case in the structure in which the UV light sources are installed on the door and the slide dock as illustrated in FIG. 15. Thus, as illustrated in FIG. 17, a power supply rail 870 may be installed on the case 810, and a power connection unit 875 may be installed at each UV light source 821b. In this case, when the slide dock 835 is drawn forward, the power connection unit 875 may be isolated from the power supply rail 870 so as to block the power supply to the UV light source 812b exposed to the outside. Besides, the position of the slide dock may be detected for an electric circuit to control whether to turn on the UV light source.

In accordance with the embodiments of the present invention, a mobile device may be mounted on the charging apparatus such that the front and rear surfaces thereof are exposed in the charging apparatus, and the UV light sources may be arranged to irradiate UV light onto the exposed front and rear surfaces of the mobile device. Thus, both surfaces of the mobile device may be sterilized at the same time, in a state where the mobile device is mounted in the charging apparatus.

While various embodiments have been described above, it will be understood to those skilled in the art that the embodiments described are by way of example only. Accordingly, the disclosure described herein should not be limited based on the described embodiments.

What is claimed is:

1. A sterilizing apparatus for sterilizing an electronic device, the sterilizing apparatus comprising:
    a dock having a top surface, a bottom surface opposite to the top surface, and a sidewall connecting the top surface and the bottom surface;
    a first light source and a second light source that have a wavelength to sterilize the electronic device and irradiate light toward the electronic device, wherein the first light source is arranged on the top surface of the dock to irradiate light toward the electronic device; and
    a charging port disposed on the top surface of the dock and providing a connection with the electronic device, and
    wherein the sterilizing apparatus further comprises a power supply trigger unit to control power to be supplied to the first light source and the second light source when the electronic device is coupled to the charging port.

2. The sterilizing apparatus of claim 1, further comprising a guide having portions disposed on sides of the charging port and configured to guide the electronic device to be connected to the charging port.

3. The sterilizing apparatus of claim 2, wherein a width of the guide decreases in a direction toward the charging port.

4. The sterilizing apparatus of claim 1, further comprising a drum positioned on the dock and protruding from the dock to provide a base for the charging port.

5. The sterilizing apparatus of claim 4, wherein the drum is rotatable about an axis, such that, when the drum is rotated, the electronic device connected to the charging port rotates together with rotation of the drum.

6. The sterilizing apparatus of claim 4, wherein the drum is oriented to place the electronic device obliquely in the charging apparatus.

7. The sterilizing apparatus of claim 4, wherein the drum includes a power supply trigger device which is triggered to supply power to the UV light source when the drum is located at a particular position.

8. The sterilizing apparatus of claim 1, further comprising a cover configured to cover a top of the charging apparatus.

9. The sterilizing apparatus of claim 8, wherein the cover includes another UV light source disposed on a surface of the cover and configured to irradiate UV light toward the electronic device.

10. The sterilizing apparatus of claim 1, wherein the dock is movable between a first position and a second position different from the first position.

11. The sterilizing apparatus of claim 1, wherein the dock is configured to move between an inner predetermined position that is on inside of the charging apparatus and a position outside the charging apparatus.

12. The sterilizing apparatus of claim 1, further comprising a power supply trigger device configured to control power to be supplied to the UV light source.

13. A sterilizing apparatus for sterilizing an electronic device, the sterilizing apparatus comprising:

a dock having a top surface, a bottom surface opposite to the top surface, and a sidewall connecting the top surface and the bottom surface;

a charging port disposed on the top surface of the dock;

a guide disposed around the charging port and configured to facilitate a placing of the electronic device into the sterilizing apparatus; and UV light sources disposed to irradiate UV light toward first and second surfaces of the electronic device, wherein the guide has a width that decreases in a direction toward the top surface of the dock.

14. The sterilizing apparatus of claim 13, further comprising a drum formed on the dock and protruding from the dock to provide a space for the charging port, the drum operating to place the electronic device to be obliquely in the charging apparatus.

15. The sterilizing apparatus of claim 13, further comprising an openable and closable door to expose or cover the charging apparatus.

16. The sterilizing apparatus of claim 15, wherein the UV light sources include a UV light source disposed on the door.

17. The sterilizing apparatus of claim 13, wherein the UV light sources include two UV light sources that are arranged in a diagonal direction.

18. The sterilizing apparatus of claim 13, further comprising a power supply trigger device configured to control power to be supplied to the UV light sources.

\* \* \* \* \*